United States Patent [19]

Seufert et al.

[11] Patent Number: 4,537,884

[45] Date of Patent: Aug. 27, 1985

[54] 2-TRIFLUOROMETHYLPHENYL (DI)THIOPHOSPHATES, AND THEIR USE FOR PEST CONTROL

[75] Inventors: Walter Seufert, Ludwigshafen; Juergen Varwig, Heidelberg; Wolfgang Seppelt, Bobenheim-Roxheim; Heinrich Adolphi, Limburgerhof, all of Fed. Rep. of Germany

[73] Assignee: BASF Aktiengesellschaft, Fed. Rep. of Germany

[21] Appl. No.: 457,184

[22] Filed: Jan. 11, 1983

[30] Foreign Application Priority Data

Jan. 16, 1982 [DE] Fed. Rep. of Germany ....... 3201227

[51] Int. Cl.³ .................. A01N 57/14; C07F 9/165
[52] U.S. Cl. .................................... 514/127; 260/948; 260/950; 514/129; 514/147
[58] Field of Search .............. 260/951, 955, 948, 950; 424/216, 217, 224

[56] References Cited

U.S. PATENT DOCUMENTS

| | | | |
|---|---|---|---|
| 3,819,755 | 6/1974 | Tarnow et al. | 260/955 |
| 3,839,509 | 10/1974 | Drabek et al. | 260/955 |
| 3,867,483 | 2/1975 | Kristiansen | 260/954 |
| 4,130,607 | 12/1978 | Arold | 260/973 |

FOREIGN PATENT DOCUMENTS 2130597 of 0000 France .
57-085395 5/1982 Japan ................... 260/955

OTHER PUBLICATIONS

Jones, "J. Amer. Chem. Soc.," vol. 69, (1947), pp. 2346-2350.
Chemical Abstracts, Band 97, Nr. 19, 8. Nov. 1982, Seite 741, Nr. 163252a, Columbus, Ohio, U.S.A. & JP-A-82 38792 (Kumiai Chemical Industry Co., Ltd.) 03.03.1982* Zusammenfassung*.
Chemical Abstracts, Band 98, Nr. 9, 28. Feb. 1983, Seite 659, Nr. 72436t, Columbus, Ohio U.S.A. & JP-A-57 85395 (Kumiai Chemical Industry Co., Ltd.) 28.05.1982* Zusammenfassung*.

*Primary Examiner*—Anton H. Sutto
*Attorney, Agent, or Firm*—Keil & Weinkauf

[57] ABSTRACT

2-Trifluoromethylphenyl (di)thiophosphates of the formula

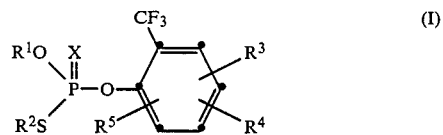

where $R^1$ is alkyl of 1 to 3 carbon atoms, $R^2$ is alkyl of 1 to 5 carbon atoms, alkoxyalkyl or alkylthioalkyl of 2 to 8 carbon atoms or cycloalkyl of 3 to 6 carbon atoms, $R^3$, $R^4$ and $R^5$ independently of one another are each hydrogen, cyano, halogen, alkoxy, alkylthio, each of 1 to 4 carbon atoms, or alkyl of 1 to 4 carbon atoms, which may be substituted by halogen or cyano, and X is oxygen or sulfur, are used for pest control.

5 Claims, No Drawings

2-TRIFLUOROMETHYLPHENYL (DI)THIOPHOSPHATES, AND THEIR USE FOR PEST CONTROL

The present invention relates to 2-trifluoromethylphenyl (di)thiophosphates, a process for their preparation and pest control agents containing these compounds as active ingredients.

German Laid-Open Application DOS No. 2,149,312 discloses that O,O-dialkyl O-(4-trifluoromethylphenyl)thionophosphates can be used as nematicides and soil insecticides.

We have found that 2-trifluoromethylphenyl (di)thiophosphates of the formula

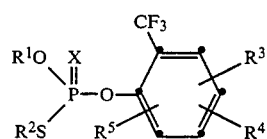
(I)

where $R^1$ is alkyl of 1 to 3 carbon atoms, $R^2$ is alkyl of 1 to 5 carbon atoms, alkoxyalkyl or alkylthioalkyl of 2 to 8 carbon atoms or cycloalkyl of 3 to 6 carbon atoms, $R^3$, $R^4$ and $R^5$ independently of one another are each hydrogen, cyano, halogen, alkyl of 1 to 4 carbon atoms, which may be substituted by halogen or by cyano, or are alkoxy or alkylthio, each of 1 to 4 carbon atoms, and X is oxygen or sulfur, effectively control pests from the classes of insects, arachnids and nematodes. Their action is superior to that of the conventional O,O-dialkyl O-(4-trifluoromethylphenyl)thionophosphates of analogous structure.

In formula I, $R^1$ is alkyl of 1 to 3 carbon atoms, eg. methyl, ethyl, n-propyl or i-propyl, $R^2$ is alkyl of 1 to 5 carbon atoms, eg. methyl, ethyl, n-propyl, i-propyl, n-butyl, sec.-butyl, i-butyl, n-pentyl, 1-methyl-n-butyl or 3-methyl-n-pentyl, alkoxyalkyl or alkylthioalkyl of 2 to 8, preferably 2 to 5, carbon atoms, eg. 2-methoxyethyl, 2-ethoxyethyl, 2-isopropoxyethyl, 2-methylthioethyl or 2-ethylthioethyl, or cycloalkyl of 3 to 6 carbon atoms, eg. cyclopentyl or cyclohexyl, and $R^3$, $R^4$ and $R^5$, which may differ, are hydrogen, cyano, halogen, eg. chlorine, bromine or fluorine, or alkyl of 1 to 4, preferably 1 or 2, carbon atoms, eg. methyl, ethyl, n-propyl or tert.-butyl, which can be substituted by halogen, eg. chlorine or bromine, or by cyano. $R^3$, $R^4$, $R^5$ may also be alkoxy or alkylthio, each of 1 to 4 carbon atoms, eg. methoxy, methylthio, ethoxy or ethylthio.

The 2-trifluoromethylphenyl (di)thiophosphates of the formula I are obtained by reacting a phosphoric acid O,S-dialkyl ester chloride of the formula

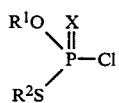
(II)

where $R^1$, $R^2$ and X have the above meanings, with a 2-trifluoromethylphenol of the formula

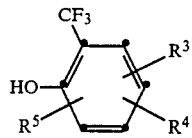
(III)

where $R^3$, $R^4$ and $R^5$ have the above meanings, in the presence or absence of an acid acceptor and in the presence or absence of a diluent, or with a salt of a 2-trifluoromethylphenol of the formula III in the presence of absence of a diluent.

The course of the reaction can be represented by the following equation:

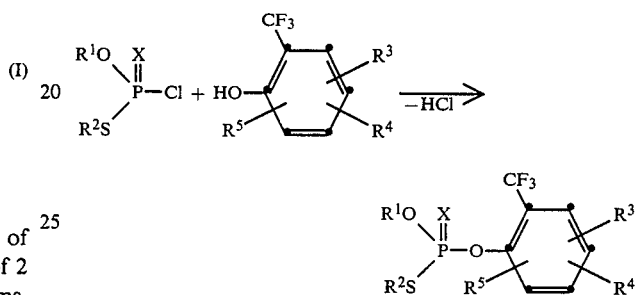

The phosphoric acid ester chloride of the formula II can be reacted with the phenol of the formula III in an organic diluent, such as acetone, acetonitrile, benzene, toluene, chlorobenzene or methyl ethyl ketone, or in a two-phase system, such as toluene/water or methylene chloride/water.

Advantageously, 1 to 2 moles of an acid acceptor are added per mole of phenol of the formula III. An excess of about 10% is preferably used. Suitable acid acceptors are bases, such as alkali metal carbonates, eg. potassium carbonate, alkali metal hydroxides, eg. sodium hydroxide, and tertiary amines, eg. triethylamine. Instead of a base and a phenol, it is also possible to react a salt of the phenol with the phosphoric acid ester chloride. Suitable salts are those of alkali metals or alkaline earth metals, or unsubstituted or substituted ammonium salts, such as alkylammonium salts, for example dimethylammonium, triethylammonium, sodium and calcium salts.

The reaction temperature can be varied within a substantial range. In general, the reaction is carried out at from 0° to 100° C., preferably from 20° to 70° C., and usually under atmospheric pressure.

The starting substances are employed in an equimolar ratio, although an excess of one or other of the reactants may bring advantages in some cases. Advantageously, 0.9 to 1.1 moles of phosphoric acid ester chloride are used per mole of phenol.

The reaction mixture is worked up in a conventional manner, for example by adding water and separating the phases. The crude products can be purified by distillation or column chromatography.

Phosphoric acid, O,S-dialkyl ester chlorides of the formula II are known and can be prepared in a conventional manner, cf. German Laid-Open Application DOS No. 2,642,982 and J. Org. Chem. 30 (1965), 3217.

The 2-trifluoromethylphenols of the formula III can also be prepared in a conventional manner, cf. J. Amer. Chem. Soc. 69 (1947), 2346.

The other processes described below also give the compounds according to the invention:

2-Trifluoromethylphenyl thiophosphates of the formula Ia can be prepared in a Arbusow reaction, by reacting phosphorous acid esters of the formula IV with sulfenyl chlorides of the formula $R^2SCl$ in accordance with the following equation:

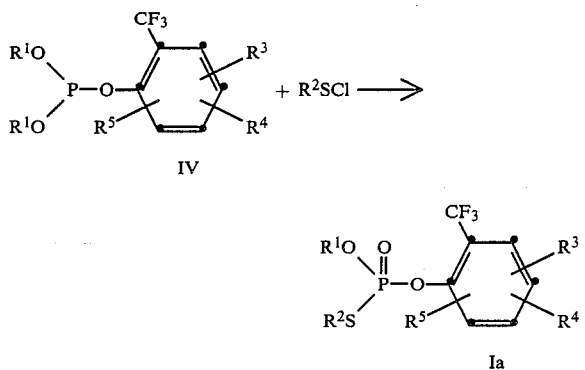

The 2-trifluoromethylphenyl thiophosphates of the formula Ia are also accessible by alkylation of phosphoric acid ester salts of the formula IV with alkylating agents of the formula $R^2Y$:

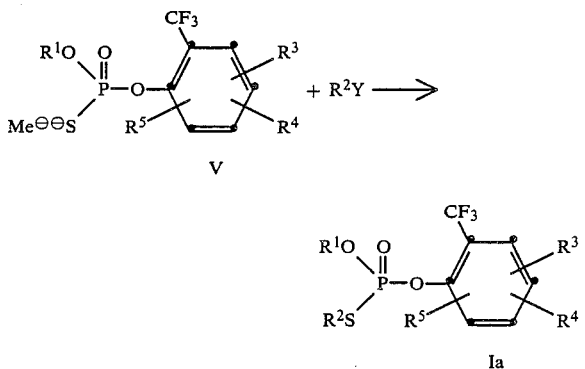

Phosphoric acid ester dichlorides of the formula VI can also be reacted with alcohols or mercaptans of the formula $R^1OH$ or $R^2SH$ to give compounds of the formula I:

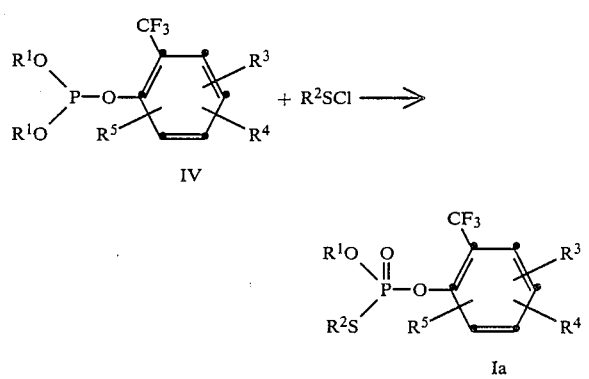

In these equations, $R^1$, $R^2$, $R^3$, $R^4$, $R^5$ and X have the above meanings, $Me^\oplus$ is a metal cation or an ammonium ion, which may be substituted by alkyl, and Y is halide, eg. iodide, bromide or chloride, or alkyl-sulfate, eg. methyl-sulfate.

EXAMPLE 1

10.1 g of phosphoric acid O-ethyl S-propylthio ester chloride were added dropwise to 8.9 g of 2-trifluoromethylphenol and 7.6 g of potassium carbonate in 100 ml of acetonitrile. The mixture was then stirred at 50° C. for 4 hours and subsequently at room temperature for 12 hours.

The solvent was then removed on a rotary evaporator, 400 ml of toluene and 100 ml of water were added to the residue, the phases were separated and the organic phase was washed with 2N sodium hydroxide solution and then with water. After the organic phase had been dried with sodium sulfate, the solvent and volatile impurities were removed at 40° C. under a reduced pressure of 0.1 mbar. 10.2 g of product of refractive index $n_D^{21} = 1.4805$ were obtained as the residue.

The following compounds were obtained by one of the above processes:

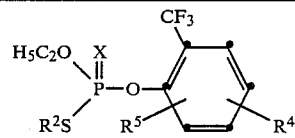

| No. | $R^2$ | X | $R^4$ | $R^5$ | $n_D$ |
|---|---|---|---|---|---|
| 1 | n-$C_3H_7$ | O | H | H | $n_D^{21} = 1.4805$ |
| 2 | s-$C_4H_9$ | O | H | H | $n_D^{21} = 1.4783$ |
| 3 | n-$C_3H_7$ | O | H | H | $n_D^{22} = 1.4773$ |
| 4 | $C_2H_5O-(CH_2)_2$ | O | H | H | $n_D^{25} = 1.4835$ |
| 5 | n-$C_3H_7$ | S | H | H | $n_D^{22} = 1.5130$ |
| 6 | s-$C_4H_9$ | S | H | H | $n_D^{21} = 1.5100$ |
| 7 | i-$C_4H_9$ | S | H | H | $n_D^{27} = 1.5085$ |
| 8 | n-$C_3H_7$ | O | 4-Br | H | $n_D^{24} = 1.5054$ |
| 9 | i-$C_4H_9$ | O | 4-Br | H | $n_D^{23} = 1.5011$ |
| 10 | n-$C_3H_7$ | S | 4-Br | H | $n_D^{22} = 1.5341$ |
| 11 | s-$C_4H_9$ | S | 4-Br | H | $n_D^{23} = 1.5307$ |
| 12 | i-$C_4H_9$ | S | 4-Br | H | $n_D^{24} = 1.5289$ |
| 13 | n-$C_3H_7$ | O | 4-Cl | H | $n_D^{20} = 1.4900$ |
| 14 | s-$C_4H_9$ | O | 4-Cl | H | $n_D^{20} = 1.4870$ |
| 15 | n-$C_3H_7$ | O | 4-Br | 6-Br | $n_D^{22} = 1.5222$ |
| 16 | n-$C_3H_7$ | S | 4-Br | 6-Br | $n_D^{21} = 1.5478$ |
| 17 | n-$C_3H_7$ | O | 4-Cl | 6-Cl | $n_D^{19} = 1.5700$ |
| 18 | s-$C_4H_9$ | O | 4-Cl | 6-Cl | $n_D^{19} = 1.5045$ |
| 19 | i-$C_4H_9$ | O | 4-Cl | 6-Cl | $n_D^{18} = 1.5045$ |

The following compounds of the formula I may be obtained analogously:

| No. | $R^1$ | $R^2$ | X | $R^3$ | $R^4$ | $R^5$ | $n_D$ |
|---|---|---|---|---|---|---|---|
| 20 | $C_2H_5$ | n-$C_3H_7$ | O | H | H | 6-Br | |
| 21 | $C_2H_5$ | n-$C_3H_7$ | O | H | H | 6-Cl | |
| 22 | $C_2H_5$ | n-$C_3H_7$ | O | H | 4-CN | H | |
| 23 | $C_2H_5$ | n-$C_3H_7$ | O | H | 4-$CH_3$ | H | |
| 24 | $C_2H_5$ | n-$C_3H_7$ | S | H | 4-Cl | H | |
| 25 | $C_2H_5$ | n-$C_3H_7$ | S | H | 4-Cl | 6-Cl | |
| 26 | $C_2H_5$ | n-$C_3H_7$ | O | H | H | H | |
| 27 | $C_2H_5$ | i-$C_3H_7$ | O | H | 4-Cl | H | |
| 28 | $C_2H_5$ | i-$C_3H_7$ | O | H | 4-Br | H | |
| 29 | $C_2H_5$ | i-$C_3H_7$ | S | H | H | H | |
| 30 | $C_2H_5$ | s-$C_4H_9$ | O | H | H | 6-Br | |
| 31 | $C_2H_5$ | s-$C_4C_9$ | O | H | 4-Br | H | |
| 32 | $C_2H_5$ | s-$C_4H_9$ | O | H | H | 6-Cl | |
| 33 | $C_2H_5$ | s-$C_4H_9$ | S | H | 4-Cl | H | |
| 34 | $CH_3$ | n-$C_3H_7$ | O | H | H | H | |
| 35 | $CH_3$ | n-$C_3H_7$ | S | H | H | H | |
| 36 | $CH_3$ | s-$C_4H_9$ | O | H | H | H | |
| 37 | $CH_3$ | s-$C_4H_9$ | S | H | H | H | |
| 38 | $CH_3$ | n-$C_3H_7$ | O | H | 4-Br | H | |

-continued

| No. | R¹ | R² | X | R³ | R⁴ | R⁵ | $n_D$ |
|-----|-----|-----|---|-----|-----|-----|-----|
| 39 | CH₃ | n-C₃H₇ | O | 6-Br | H | H | |
| 40 | CH₃ | n-C₃H₇ | O | H | 4-Cl | H | |
| 41 | CH₃ | n-C₃H₇ | O | H | H | 6-Cl | |

The 2-trifluoromethylphenyl-(di)thiophosphates of the formula I are suitable for effectively combating pests from the classes of insects, Arachnida and nematodes. They may be used as pesticides for protecting crops, and in the hygiene, stores protection and veterinary sector.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Spargonothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarius, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monacha, Pieris brassicae,* and *Aporia crataegi;* examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotetra nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinta tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Byrobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ester sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylyated octylphenol and ethoxylated nonylphenol, alkylphenol polyglycol ethers, tributylphenyl polyglycol ethers, alkylaryl polyester alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbital esters, lignin, sulfite waste liquors and methyl cellulose.

Powders, dusts broadcasting agents may be prepared by mixing or grinding the active ingredients with a solid carrier.

Examples of formulations are given below.

I. 50 parts by weight of compound no. 1 is intimately mixed with 95 parts by weight of particulate kaolin. A dust is obtained containing 5% by weight of the active ingredient.

II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 4 is dissolved in a mixture consisting of 90 parts by weight of xylene, 6 parts by weight of the adduct of 8 to 10 moles of ethylene oxide with 1 mol of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

IV. 20 parts by weight of compound no. 13 is dissolved in a mixture consisting of 60 parts by weight of cyclohexanone, 30 parts by weight of isobutanol, 5 parts by weight of the adduct of 7 moles of ethylene oxide with 1 mole of isooctylphenol, and 5 parts by weight of the adduct of 40 moles of ethylene oxide with 1 mole of castor oil.

V. 80 parts by weight of compound no. 19 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bore, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90%, by weight of active ingredient.

The amount of active ingredient in the ready-to-use formulations may vary within a wide range; it is generally from 0.0001 to 10%, preferably from 0.01 to 1%.

The active ingredients may also be successfully used in the ultra-low volume method, where it is possible to apply formulations containing more than 95 wt% of active ingredient, or even the 100% active ingredient.

In the open, application rates are from 0.2 to 10, and preferably from 0.5 to 2.0, kg of active ingredient per hectare.

There may be added to the individual active ingredients (if desired, immediately before use (tankmix)) oils of various types, herbicides, fungicides, other pesticides and bactericides. These agents may be added to the active ingredients according to the invention in a weight ratio of from 1:10 to 10:1.

Examples of active ingredients which may be admixed are as follows:
1,2-dibromo-3-chloropropane, 1,3-dichloropropene, 1,3-dichloropropene+1,2-dichloropropane, 1,2-dibromomethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl, N', N'-dimethyl-N-[(methylcarbamoyl)-oxy]-1-thiooxamidate, N-(2methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothoate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)o-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl(3)]-methyldithiophosphate, O,O-dimethyl-S-[2-methoxy-1,3,4-thiadiazol-5-onyl-(4     )-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphonate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, alpha-hexachlorocyclohexane, 1,1-di-(p-methoxyphenyl)-2,2,2-trichloroethane, 6,7,8,9,10,10-hexachloro-1,5,5a6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, alpha-cyano-3-phenoxybenzyl(±)-cis,trans-2,2-dimethyl-3-(2,2-dichlorovinyl)-cyclopropane carboxylate, (s)-alpha-cyano-3-phenoxybenzyl-cis(1R,3R)-2,2-dimethyl-3-(2,2-dibromovinyl)-cyclopropane carboxylate, 3,4,5,6-tetrahydrophtalimidoethyl-DL-cis,trans-chrysanthemate, 2-methyl-5-(2-propynyl)-3-furylmethyl-chrysanthemate, and alpha-cyano-3-phenoxybenzyl-alpha-isopropyl-4-chlorophenylacetate.

The following examples illustrate the biological action of the compounds. The agent used for comparison purposes was O,O-diethyl-O-(4-trifluoromethylphenyl)-thionophosphate (disclosed in Germain Laid-Open Application DE-OS No. 2,149,312).

The active ingredients are numbered as in the foregoing table.

EXAMPLE 1

Contact action and effect of ingested food on caterpillars of the diamondback moth (*Plutella maculipennis*)

Leaves of young cabbage plants were dipped for 3 seconds in aqueous emulsions of the active ingredients, and, after briefly having allowed excess liquid to drip off, were placed on a moist filter paper in a Petri dish. 10 caterpillars of the 4th stage were then placed on the leaves. The action was assessed after 48 hours.

In this test, active ingredients nos. 1, 2, 3, 4, 5, 6, 7, 8, 9, 10, 11, 12, 13, 14, 15, 16, 17, 18 and 19 had a better action than the prior art compound.

EXAMPLE 2

Contact action on mosquito larvae (*Aedes aegypti*)

Formulations of the active ingredients were added to 200 ml to tapwater; 20 to 30 mosquito larvae of the 4th larval stage were then introduced. The temperature was kept at 20° C. The action was assessed after 24 hours.

In this test, active ingredients nos. 2, 5, 6, 8, 10, 11 and 18 had a better action than the prior art compound.

EXAMPLE 3

Contact action on oriental cockroaches (*Blatta orientalis*)

The bottom of 1 liter preserving jars was lined with acetonic solutions of the active ingredients. After the solvent had evaporated, 5 adult cockroaches were introduced into each jar. The kill rate was determined after 48 hours.

In this test, active ingredients nos. 1, 2, 3, 4, 5, 8, 9, 10, 11, 17 and 18 had a better action than the comparative agent.

EXAMPLE 4

Contact action on ticks (*Ornithodorous moubata*)

The experiment was carried out on young ticks which had sucked blood only once. Paper bags, each containing 5 animals, were dipped for 5 seconds in the aqueous active ingredient formulation. The bags were then suspended. The temperature was kept at 25° to 26° C. The kill rate was determined after 48 hours.

In this test, active ingredients nos. 1, 2, 3, 4, 8, 9, 15, 17 and 19 had a better action than the comparative agent.

EXAMPLE 5

Action on root-knot nematodes (*Meloidogyne incognita*)

30 ml of aqueous formulations of the active ingredients was intimately mixed with 200 mg of mold heavily infested with *Meloidogyne incognita*. The mold was then filled into plastic pots and a tomato seedling planted therein. The temperature was kept now lower than 22° C.

The roots were checked for root-knots after 6 to 8 weeks.

In this test, active ingredients nos. 1, 2, 3, 4, 5, 6, 7, 9, 10, 11, 12 and 13 had a superior action.

EXAMPLE 6

Action on spider mites (*Tetranychus telarius*)

Potted bush beans which had developed the first pair of true leaves and were under heavy attack from spider mites (*Tetranychus telarius*) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

In this test, active ingredients nos. 8, 9, 10, 11, 15, 18 and 19 had a better action than the comparative agent.

EXAMPLE 7

Contact action on cotton stainers (*Dysdercus intermedius*)

Petri dishes 10 cm in diameter were lined with 1 ml of acetonic solutions of the active ingredients. After the solvent had evaporated, 20 larvae of the penultimate stage were placed in the dishes, and the effect was registered after 24 hours.

In this test, active ingredients nos. 1, 2, 3, 4, 5, 6, 7, 8, 9, 10, 11, 15, 17, 18 and 19 had a superior action.

EXAMPLE 8

Systemic action on caterpillars (*Prodenia litura*)

200 ml of quartz sand was filled into 250 ml plastic beakers, which were then placed in 8-vessel pallets. 5 Indian corn grains were introduced into each beaker (about 1 cm beneath the surface). Each beaker was then moistened with 50 ml of water and covered with a fitting transparent plastic hood. After 8 days, the hoods were removed and treatment was effected after 10 days. Each beaker was watered with 40 ml of the aqueous active ingredient formulations, and, after a further day, 50 ml of dry quartz sand was added as a cover to each beaker. The purpose of this sand cover is to prevent the test animals from coming into contact with the treated surface.

Plastic cylinders 7 cm in diameter were placed on each beaker, 5 caterpillars in the 3rd larval stage were introduced, and the cylinders were capped with a wire gauze cover. Eating and mortality in the vessels were assessed after 4 days. Not only was a systemic poisoning action registered-eating was also prevented.

In this test, active ingredients nos. 1, 2, 3, 4, 5, 6, 7, 8, 9, 10, 11, 15, 16, 17, 18 and 19 had a better action than the comparative agent.

We claim:

1. A 2-trifluoromethylphenyl (di)thiophosphate of the formula $$\begin{array}{c} R^1O \\ \diagdown \\ R^2S \end{array} \overset{X}{\underset{\parallel}{P}} - O - \underset{R^5}{\underset{|}{\bigcirc}} \overset{CF_3}{\underset{}{}} - R^4, \quad (1)$$

where $R^1$ is alkyl of 1 to 3 carbon atoms, $R^2$ is alkyl of 1 to 5 carbon atoms, alkoxyalkyl or alkylthioalkyl of 2 to 8 carbon atoms or cycloalkyl of 3 to 6 carbon atoms, $R^4$ and $R^5$ independently of one another are each hydrogen, halogen or alkyl of 1 to 4 carbon atoms, and X is oxygen or sulfur.

2. A 2-trifluoromethylphenyl (di)thiophosphate of the formula I as defined in claim 1, wherein $R^1$ is alkyl of 1 to 3 carbon atoms, $R^2$ is alkyl of 3 to 4 carbon atoms or ethyloxyethylene and $R^4$ and $R^5$ independently of one another are each hydrogen, chlorine or bromine.

3. A 2-trifluoromethylphenyl (di)thiophosphate of the formula I as defined in claim 1, where $R^1$ is ethyl, $R^2$ is alkyl of 3 to 4 carbon atoms or ethyloxyethylene and $R^4$ and $R^5$ independently of one another are each hydrogen, chlorine or bromine.

4. A process for combating pests, wherein an effective amount of a 2-trifluoromethylphenyl (di)thiophosphate of the formula I as defined in claim 1 is allowed to act on pests and/or their habitat.

5. A pesticide containing inert additives and an effective amount of a 2-trifluoromethylphenyl (di)thiophosphate of the formula I as defined in claim 1.

* * * * *